United States Patent [19]

Chalk et al.

[11] Patent Number: 5,274,171

[45] Date of Patent: Dec. 28, 1993

[54] PROCESS FOR THE PALLADIUM CATALYZED COUPLING OF A DIAZONIUM SALT WITH AN OLEFINIC BOND

[75] Inventors: Alan J. Chalk, Kinnelon; Joseph A. Virgilio, Wayne; Laszlo Wertheimer; Theresa B. Wertheimer, both of Whippany, all of N.J.

[73] Assignee: Givaudan-Roure Corporation, Clifton, N.J.

[21] Appl. No.: 823,791

[22] Filed: Jan. 22, 1992

[51] Int. Cl.$^5$ .................. C07C 57/42; C07C 57/44; C07C 69/618
[52] U.S. Cl. .................................. 560/104; 534/565; 562/495
[58] Field of Search .............. 534/565; 560/104; 562/495

[56] References Cited

U.S. PATENT DOCUMENTS 4,145,362  3/1979  Brepoels et al. ............ 562/495 X
4,970,332  11/1990  Caskey ......................... 560/552

OTHER PUBLICATIONS

K. Shank, "Preparation of Diazonium Groups" in The Chemistry of Diazonium and Diazo Groups, Part 2, S. Patei, Ed., John Wiley, N.Y. (1978) pp. 645-657.
R. Heck, "Palladium Reagents In Organic Synthesis", (1985), Academic Press, N.Y., pp. 287-290, 446.
K. Kikukawa et al. IV, Tetrahedron, 37 (1981), pp. 31-36.
K. Kikukawa et al., I Chem. Let. (1977), pp. 159-162.
K. Kikukaw et al., II Bull. Chem. Soc. Jap., 52 (1979), pp. 2609-2610.
K. Kikukawa et al., III Chem. Let. (1980), pp. 551-552.
K. Kikukawa et al., IV J. Org. Chem. 46 (1981), pp. 4885-4888.

*Primary Examiner*—Floyd D. Higel
*Attorney, Agent, or Firm*—George M. Gould; George W. Johnston

[57] ABSTRACT

A "one-pot" process for the palladium catalyzed coupling of a diazonium salt with an olefinic bond, in the aqueous medium in which the diazonium salt is made, by employing a carboxylic acid as a solvent. Arylacrylic acids and their esters, e.g. the cinnamates, can be produced at low catalyst concentration without first isolating the diazonium salt. The process is applied to the synthesis of 2-ethylhexyl p-methoxycinnamate.

8 Claims, No Drawings

PROCESS FOR THE PALLADIUM CATALYZED COUPLING OF A DIAZONIUM SALT WITH AN OLEFINIC BOND

BACKGROUND OF THE INVENTION

1. Field of the Invention

The invention relates to a process for making arylacrylic acids and their esters by the palladium catalyzed coupling of a diazonium salt with an olefinic bond.

2. Background Art

Arylacrylic acid derivatives, particularly the cinnamates, have ultraviolet light-absorbing properties which make them valuable for use as UV light-absorbing agents. One of the most important UV absorbers sold in the United States and throughout the world is 2-ethylhexyl p-methoxycinnamate (octyl methoxycinnamate). Octyl methoxycinnamate is the most widely used active ingredient in all major sunscreen and suntanning lotions throughout the world and is a category I sunscreen as defined by the Tentative Final Monograph for Sunscreens. (See 21 CFR Part 352, Docket 78N0038.)

One of the most common routes to arylacrylic acid derivatives such as octyl methoxycinnamate is to react an aryl aldehyde with an acetate as set forth in Scheme I.

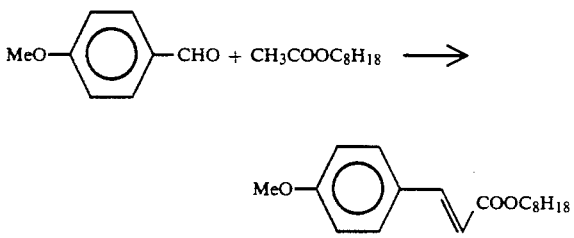

SCHEME I

This is the method by which octyl methoxycinnamate is made on a commercial basis. The major drawback of the method is the cost of the starting aldehyde, anisaldehyde. Consequently, an alternative synthesis that uses a less expensive starting material has been sought.

One available alternative is the use of the so-called "Heck reaction" which involves coupling an organopalladium intermediate with an olefin. The synthesis has been applied to octyl methoxycinnamate wherein the organopalladium intermediate is generated from p-methoxyphenyliodide and subsequently coupled with the acrylic ester, ethylhexyl acrylate, in the presence of a tertiary amine (U.S. Pat. No. 4,970,322). The drawback of the reaction when applied to the synthesis of octyl methoxycinnamate, is again the expense of the starting material p-methoxyphenyliodide. To overcome the problem, the inventors in U.S. Pat. No. 4,970,322 generated p-methoxyphenyliodide from the more economical p-anisidine via a diazonium salt. Once neutralized, the iodide can be separated and used in the Heck reaction as described above. The overall process is illustrated in Scheme II.

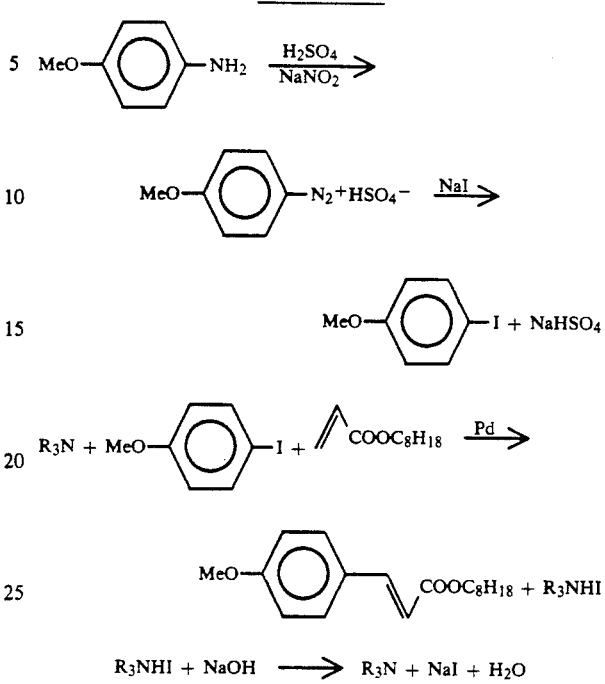

The economic viability of this process requires that the iodide and the tertiary amine be efficiently recycled. The disadvantage is that four reaction steps are required instead of one and that losses occur in each step. Clearly, it would be desirable to react the diazonium salt directly with the acrylic acid ester to eliminate a number of steps.

In theory, the palladium catalyzed coupling of an aromatic ring with an olefinic bond using a diazonium salt as the starting material is feasible. The literature on the reaction has been reviewed (R. F. Heck, "Palladium Reagents in Organic Synthesis", Academic Press, 1985, p.287-290) for a number of model systems, albeit not for the potential synthesis of octyl methoxycinnamate. As a practical matter, however, no successful commercial process utilizing the diazonium salt has been developed. This is due primarily to the fact that the most commercially feasible way of preparing the salt is in an aqueous solution which is generally immiscible with the olefinic substrate. This immiscibility results in either no reaction or a greatly diminished rate of reaction. The latter has many disadvantages, the most significant of which is that side reactions, such as hydrolysis of the diazonium salt to the phenol, can efficiently compete with the coupling reaction.

What emerges from the prior art is that attempts to overcome the immiscibility problem by the use of organic solvents which had some water miscibility, were only moderately successful. It was found that improved yields could be achieved only if the diazonium salt was first isolated as the tetrafluoborate salt and then separately reacted with the olefin under anhydrous conditions. Expense and safety considerations connected with the use of fluoroboric acid and the undesirability and safety considerations of isolating the diazonium salt make such a route commercially unfeasible.

This need to exclude water from the coupling reaction led to an alternative procedure where the diazonium salts were made in the absence of water. t-Butyl nitrite was used to form the diazonium moiety rather than sodium nitrite which requires aqueous media. (K. Kikukawa et al., J. Org. Chem., 46, (1981), 4885.) While such a method is suitable for a laboratory synthesis, it is not suitable for commercial manufacture.

An additional disadvantage of the prior art processes is that they all require relatively large amounts of the palladium catalyst, i.e., from about 1.0 mole % to about 10 mole % (see Heck Supra; K. Kikukawa et al., Tetrahedron, 37 (1981)31). The values refer to the amount of catalyst with respect to the amine. At the 2 mole % level, even when the catalyst is recovered and recycled, the catalyst cost becomes equivalent to the total cost of all other materials used. These values are excessively high for an economically viable commercial process, particularly for the manufacture of a UV-light absorbing agent.

Thus the prior art does not teach or suggest a palladium catalyzed addition of a diazonium salt to a double bond which would have any commercial potential. The need for anhydrous conditions and an excessive amount of palladium catalyst to obtain reasonably high yields, make all such processes prohibitively expensive.

SUMMARY OF THE INVENTION

This invention provides a "one-pot" process for the palladium catalyzed coupling of a diazonium salt with an olefinic bond, in the aqueous medium in which the diazonium salt is made, by employing a carboxylic acid as a solvent. Arylacrylic acids and their esters, e.g. the cinnamates, can be produced in unexpectedly high yields, using low concentrations of palladium catalysts, without first isolating the diazonium salt. The process provides a competitive method for the commercial synthesis of the widely used UV absorber, 2-ethylhexyl p-methoxycinnamate.

DESCRIPTION OF THE PREFERRED EMBODIMENTS

The process of the invention may be applied to a wide range of arylamines, i.e., an amine having an NH2 group on an aromatic or heteroaromatic ring, which give diazonium salts on treatment with nitrous acid. (See "The Chemistry of Diazonium and Diazo Groups", Part 2, Saul Patai, editor, John Wiley, N.Y. (1978) pgs 645-657. Heteroaromatic should be understood to mean an aromatic group having 5 to 6 atoms in a ring, 1 to 3 of which are heteroatoms contained in the aromatic ring, selected from oxygen, sulfur or nitrogen, with the remaining atoms being carbon atoms, the group being sufficiently unsaturated to provide aromatic character to the ring.) Such amines may be represented by the general formula Ar—NH2 wherein Ar represents an aromatic or a heteroaromatic group such as phenyl, naphthyl, biphenyl, benzofuranyl, dibenzofuranyl, pyridyl, imidazyl and the like. The aromatic or heteroaromatic ring containing the NH2 group may also contain additional substituents such as —R, —COOH, —COOR, —CONH2, —CONHR, —CONR2, —COR, —SO3H, —SO3R, —OR, —CN, —NO2 and —X wherein R represents a linear or branched alkyl group $C_nH_{2n+1}$ where n is 1-6, or phenyl and X represents a halogen. There are no restrictions on the regiochemical relationship between these substituents and NH2. Preferred amines are those where Ar—NH2 represents a substituted aniline of the formula

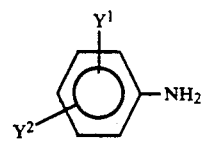

wherein $Y^1$ and $Y^2$ may be the same or different and are selected from the above named group of substituents or may be —H.

The preferred olefinic substrates are acrylic acid and its esters, and substituted acrylic acids and their esters and may be represented by the formula $CH_2=C(Z)COOR^1$ wherein Z represents —$R^2$ or —$CH_2COOR^3$ such that $R^1$, $R^2$ and $R^3$ may be the same or different and represent —H or an alkyl group —$C_nH_{2n+1}$ where n=0-20 and the alkyl group may be linear or branched. Especially preferred substrates are acrylic acid and its esters, i.e., those olefinic substrates wherein Z on the above formula represents —H.

The overall process of the invention can be represented by Scheme III.

SCHEME III

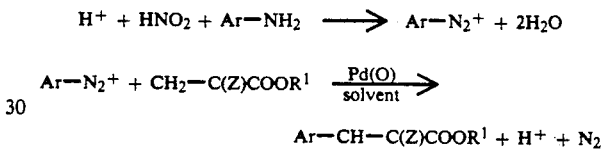

$Ar-CH-C(Z)COOR^1 + H^+ + N_2$

One advantage of the present invention is that the amine is converted to its diazonium salt in an aqueous environment which is the least costly and most practical method of preparing a diazonium salt. The nitrous acid used to prepare the diazonium salt may be generated by any standard method but is preferably produced by the reaction of a metal nitrite such as sodium or potassium nitrite and a mineral acid such as sulfuric acid. The amount of nitrous acid needed to generate the diazonium salt is generally that required by the stoichiometry, i.e., one mole of nitrous acid per mole of amine.

Sodium nitrite is preferred as the metal nitrite and sulfuric acid as the mineral acid. The amount of acid may range from 1 to 5 moles per mole of amine with 1 to 2 moles being preferred. It is preferred to keep the volume of the aqueous solution to a minimum in order to keep the total reaction volume to a minimum and thereby improve productivity. For this reason the acid is preferably added as a 98% solution. Some water is also required to dissolve the sodium nitrite. For 1 mole of sodium nitrite per mole of amine the amount of added water may be in the range of about 80 to 500 g, an optimum range being 100 to 300 g.

The ratio of the olefin to the amine may be a molar equivalent or an excess of either reagent. In general it is preferred to use the olefin in excess. In the case of acrylic acid or a substituted acrylic acid, a large excess, up to 10 moles per mole of amine, may be used since it will also function as a solvent. For other olefins, a slight excess may be used. The amount of olefin:amine is therefore generally in the range 1:1 to 2:1, preferably in the range 1:1 to 1.5:1.

As mentioned above, the use of a carboxylic acid as solvent is critical to the success of the process. The use of the acid apparently increases the miscibility of the olefinic substrate and the aqueous reactants. Preferred solvents are carboxylic acids of the type $R^4$—CH$_2$COOH wherein $R^4$=H, Cl, CH$_3$ or C$_2$H$_5$. The solvent may be used in an amount of 200–1000 mL/mole of amine with a preferred range of 400–700 mL/mole of amine. In order to keep the total reaction volume to a minimum it is preferred to use a minimum amount of solvent. Acetic acid is suitably used as the solvent for the lower molecular weight olefins such as methyl acrylate. For the longer chain olefins such as 2-ethylhexyl acrylate it is preferred to use propionic acid since large volumes of acetic acid, e.g., 1000–3000 mL/mole of amine, are required to achieve rapid reaction. For 2-ethylhexyl acrylate the amount of propionic acid required may be as little as 450 ml. Although carboxylic acids are the best solvents for the reaction, additional solvents which are not acids may be used in admixture with them to improve the miscibility of the two phases. Thus a combination of acetic acid and ethylacetate may be more effective than acetic acid alone. Many co-solvents are unsuitable however, e.g., acetonitrile, methanol, toluene, diglyme and methylformamide. Where miscibility is only partial, i.e., where two phases exist, rapid stirring is essential for a high rate of reaction.

Palladium in the form of a salt or a complex in either the divalent or zero valent state is used as catalyst. The catalyst should be soluble in aqueous or organic media. Preferred salts and complexes are sodium chloropalladite (Na$_2$PdCl$_4$), palladium acetate (Pd(OAc)$_2$), benzonitrile palladium chloride ((C$_6$H$_5$CN)$_2$PdCl$_2$), palladium nitrate ((Pd(NO$_3$)$_2$), dibenzylidene acetone palladium (O) etc. The last named complex is especially preferred since it is readily soluble in organic media and has a large molecular weight which facilitates accurate weighing. Finely divided palladium, preferably supported on charcoal is also suitable but less so than soluble forms of palladium. While the palladium catalyst may be used in a range of from 0.05 to 5.0 mole % based on the amine, it is preferred to use the minimum amount of palladium necessary to product high yields of product. The range of 0.05 to 1.0 mole % is preferred for this reason.

Nitric oxide appears to act as a catalyst poison and therefore, after formation of the diazonium salt, it is preferred to eliminate any excess nitrous acid before addition of the catalyst. Nitrous acid may be removed by any method that does not interfere with the catalyst. A suitable method is the addition of a primary amine, such as t-butylamine, or an amide, such as propionamide, to destroy the excess nitrous acid.

Where the stability of the olefin may be of concern, e.g., polymerization may occur, a small amount of an antioxidant such as butylated hydroxytoluene may be added.

ILLUSTRATION OF THE PREFERRED EMBODIMENTS

Details of the application of the invention are implicit in the following examples which illustrate the embodiments but should not be construed as limiting. Examples 1 to 12 illustrate the use of 4-methoxyaniline (p-anisidine) as the amine substrate. Examples 13 to 33 show that the reaction may be applied to a variety of amine substrates. Examples 34 to 37 illustrate the use of olefinic substrates which are not a part of the preferred embodiments.

EXAMPLES 1 AND 2

Examples 1 and 2 illustrate the use of methyl acrylate as the olefin and acetic acid as solvent. Example 2 shows that the amount of palladium catalyst can be reduced by one-third with only a 7% reduction in yield.

EXAMPLE 1 p-Anisidine (12.3 g) was dissolved in 55 ml acetic acid and 15 ml water and cooled to 10° C. 98% Sulfuric acid (15 g) was added slowly with agitation while cooling the reaction vessel, a 500 ml three necked round bottom flask equipped with stirrer, thermometer, dropping funnel and cooling bath. Sodium nitrite (6.9 g dissolved in 20 ml water) was then added at 0°–2° C. over one hour while stirring. Excess nitrous acid was then neutralized by the addition of 0.05 g t-butylamine. After 10 minutes, palladium (O) dibenzylidene acetone (Pd(dba)$_2$, 0.15 g) was added followed by methyl acrylate (12.9 g) and butylated hydroxytoluene (0.03 g). The cooling bath was then removed and the temperature allowed to slowly reach ambient conditions (25° C.). After 22 hours of stirring, the acid was neutralized with excess 10% sodium hydroxide solution (aqueous) and the mixture allowed to separate. The aqueous layer was separated and extracted twice with 20 ml portions of ethyl ether. The ether layers were combined with the organic phase, concentrated on a rotary evaporator to remove the ether and distilled to give 19.0 g of methyl p-methoxycinnamate (99% yield, purity 95% by GC).

EXAMPLE 2

Example 1 was repeated except that 0.10 g of Pd(dba)$_2$ was used. A yield of 92% product was obtained.

EXAMPLES 3–7

Examples 3 to 7 illustrate the use of ethylhexyl acrylate as the olefin with acetic acid as the solvent. Increasing the amount of acetic acid in Example 4 relative to Example 3 shows a yield increase. Example 5 illustrates the beneficial effect of using ethyl acetate as a co-solvent with acetic acid. Examples 6 and 7 illustrate the use of varying amounts of palladium-on-charcoal as the catalyst.

EXAMPLE 3

Example 2 was repeated except that 2-ethylhexyl acrylate (27.6 g) was substituted for methyl acrylate and the volume of acetic acid was 110 ml. A yield of 40% 2-ethylhexyl p-methoxycinnamate was obtained.

EXAMPLE 4

Example 3 was repeated except that the volume of acetic acid was increased to 275 ml acetic acid. The yield of 2-ethylhexyl p-methoxycinnamate increased to 90%.

EXAMPLE 5

Example 3 was repeated except that the acetic acid was reduced to 50 ml and ethyl acetate (60 ml) was added additionally. A yield of 79% was obtained.

EXAMPLE 6

Example 1 was repeated except that the catalyst [Pd(dba)$_2$] was replaced by 2.4 g of 5% palladium on charcoal and the reaction mixture was allowed to stir for 96 hours before work up. A yield of 47% was obtained.

EXAMPLE 7

Example 6 was repeated but using 10 g of palladium on charcoal and stirring for 120 hours. A yield of 81% was obtained.

EXAMPLES 8-11

Examples 8 to 11 illustrate the use of propionic acid as the solvent. Ethylhexyl acrylate is again used as the olefin. In these examples the amount of palladium catalyst was varied, the levels being close to the optimum amount.

EXAMPLE 8 p-Anisidine (123 g), propionic acid (200 ml) and water (250 ml) were mixed in a 5 liter reaction flask and cooled to 0° C. Sulfuric acid 98% (202 g) was added gradually with cooling followed by the addition of sodium nitrite (69 g) dissolved in 200 ml water over a 50 minute period. The stirring was continued for a further one hour at 0°-2° C., t-Butylamine (0.5 g) was then added. After an additional 15 minutes of stirring Pd(dba)$_2$ (1.0 g) and propionic acid (250 ml) were added. 2-Ethylhexyl acrylate (276 g) was then added over a period of 10 minutes while maintaining the temperature at 0° C. The reaction was then allowed to warm to room temperature and stirred for 24 hours. Sodium hydroxide (333 g of 30% solution) was added and after 10 minutes the lower aqueous layer was separated and extracted twice with ether (200 ml). The ether layers were combined and evaporated. The residue was combined with the organic layer and distilled to give separate fractions of propionic acid, excess ethylhexyl acrylate and 273 g of 2-ethylhexyl p-methoxycinnamate (94.0% yield).

EXAMPLE 9

As example 8 except that the amount of t-butylamine was doubled and added in two 0.5 g portions 15 minutes apart, the amount of catalyst was halved (0.5 g) and the amount of ethylhexyl acrylate was decreased to 1.0 mole. The 2-ethylhexyl p-methoxycinnamate was obtained in 98.8% yield.

EXAMPLE 10

As example 9 except that the amount of catalyst was reduced to 0.375 g. After 18 hours 2-ethylhexyl p-methoxycinnamate was obtained in a yield of 92.9%.

EXAMPLE 11

As example 9 except that the amount of catalyst was reduced to 0.25 g. After 30 hours, 2-ethylhexyl p-methoxycinnamate was obtained in 87.3% yield.

EXAMPLE 12, 13

Examples 12 and 13 illustrate the use of acrylic acid as the olefin substrate.

EXAMPLE 12

Anisidine (12.3 g) was dissolved in 30 ml acetic acid and 25 ml water and cooled to 10° C. 98% Sulfuric acid (10 ml) was added with cooling. Sodium nitrite (6.9 g in 20 ml water) was then added at 0°-2° C. over 1 hour with stirring. t-Butylamine (0.05 g) was then added and after 10 minutes, Pd(dba)$_2$ (1.0 g) and 0.07 g of 1,2-bis(-diphenylphosphino)ethane (diphos) in 50 ml ethyl acetate were added. Acrylic acid (10.3 ml) was then added slowly over 10 minutes. The reaction mixture was allowed to warm to room temperature. After 22 hours under nitrogen, the mixture was neutralized with 30% sodium hydroxide solution (33 g) diluted with 500 ml water. The aqueous solution was separated, neutralized with 10% sulfuric acid to give 12 g of p-methoxycinnamic acid as a solid precipitate which was filtered off (m.p. 165°-170° C.) (67.4% yield).

EXAMPLE 13

0.2 Mole sulfanilic acid (34.6 g) was dissolved in 30 ml sulfuric acid (67%) and cooled to 0°-10° C. in an ice bath. 0.2 Mole sodium nitrite (13.8 g) was dissolved in 40 ml water and added slowly to the above over one hour while cooling to below 10° C. After a further hour, t-butylamine (0.2 g) was added and the mixture stirred for ten minutes. Catalyst (Pd(dba)$_2$, 0.2 g) dissolved in 0.3 mole acrylic acid (20 ml) was then added and the temperature allowed to slowly rise to ambient. After 24 hours the product was worked up by adding 100 ml 30% NaOH and 75 ml water. The black aqueous solution was extracted twice with 20 ml ether and then neutralized with 33% sulfuric acid until slightly acidic. A grey precipitate was filtered off and washed twice with 10 ml portions of water and twice with 10 ml portions of acetone. On drying, 25.7 g (56.0% yield) of product was obtained which was identified by proton and C$^{13}$ NMR as 3-(4-sulfophenyl)-2-propenoic acid.

EXAMPLES 14-37

Examples 14 to 37 are listed in Table 1. These reactions were carried out at one-half the scale of example 8 using 0.5 mole of the amine listed in place of anisidine. All other quantities were halved except for the t-butylamine wherein 0.5 g was used. The liquid products were distilled (b.p. given), the solids were crystallized from a suitable solvent (methanol) and their m.p.'s recorded. Unoptimised yields are given. In each example where the reported yield is below 50%, this is the result of a single run in which the phenol was the other major product.

TABLE I

| Example | Amine | Olefin | Yield % | B.P. °C./mmHg or m.p. °C. |
|---|---|---|---|---|
| 14 | MeOOC—⟨◯⟩—NH$_2$ | Ethylhexyl acrylate | 82 | 188/0.5 |

TABLE I-continued

| Example | Amine | Olefin | Yield % | B.P. °C./mmHg or m.p. °C. |
|---|---|---|---|---|
| 15 | 2-NH₂, 1-COOMe benzene | Ethylhexyl acrylate | 88 | 187/0.7 |
| 16 | 4-NC-C₆H₄-NH₂ | Ethylhexyl acrylate | 79 | 182/0.5 |
| 17 | 4-H₂NC(O)-C₆H₄-NH₂ | Ethylhexyl acrylate | 68 | 127–8 (mp) |
| 18 | 2-Cl-C₆H₄-NH₂ | Ethylhexyl acrylate | 87 | 167/0.5 |
| 19 | 4-Cl-C₆H₄-NH₂ | Ethylhexyl acrylate | 81 | 173/0.5 |
| 20 | 4-HOOC-C₆H₄-NH₂ | Ethylhexyl acrylate | 58 | 142–3 (mp) |
| 21 | 4-HO₃S-C₆H₄-NH₂ | Ethylhexyl acrylate | 66 | >300 (mp) |
| 22 | 4-CH₃C(O)-C₆H₄-NH₂ | Ethylhexyl acrylate | 69 | 188/0.7 |
| 23 | 4-F-C₆H₄-NH₂ | Ethylhexyl acrylate | 92 | 155/1.0 |
| 24 | C₆H₅-NH₂ | Methyl acrylate | 57 | 87/0.7 |
| 25 | 2-OCH₃, 3-NH₂ dibenzofuran | Methyl acrylate | 91 | 123–124 (mp) |
| 26 | 4-O₂N-C₆H₄-NH₂ | Ethylhexyl acrylate | 56 | 198/1.0 |
| 27 | 2-SO₃H, 4-H₃CO, 1-NH₂ benzene | Ethylhexyl acrylate | 57 | >280 (mp) |

TABLE I-continued

| Example | Amine | Olefin | Yield % | B.P. °C./mmHg or m.p. °C. |
|---|---|---|---|---|
| 28 | H3CO—⟨C6H4⟩—NH2 | Dimethyl itaconate | 62 | 190/2.0 |
| 29 | ⟨C6H5⟩—NH2 | Methyl methacrylate | 11 | 85/0.5 |
| 30 | H3CO—⟨C6H4⟩—NH2 | Methyl methacrylate | 49 | 120/1.0 |
| 31 | Et—⟨C6H4⟩—NH2 | Ethylhexyl acrylate | 87 | 207/4.0 |
| 32 | Et-CH2—⟨C6H4⟩—NH2 | Ethylhexyl acrylate | 36 | 190/2.0 |
| 33 | OCH3-⟨C6H4⟩—NH2 | Ethylhexyl acrylate | 92 | 205/2.0 |
| 34 | ⟨C6H5⟩—NH2 | Methyl vinyl ketone | 22 | 90/0.5 |
| 35 | ⟨C6H5⟩—NH2 | Acrylonitrile | 1 | 85/1.0 |
| 36 | ⟨C6H5⟩—NH2 | Methacrylonitrile | 8 | 100/1.0 |
| 37 | ⟨C6H5⟩—NH2 | Acrylamide | 3 | 144–146 (mp) |

We claim:

1. A process for the preparation of an arylacrylic acid or its esters which comprises:
   a) converting an arylamine having the formula Ar—NH2 wherein Ar represents an aromatic or heteroaromatic group,
   to a diazonium salt, with a stoichiometric amount of nitrous acid, in an aqueous media, and b) reacting said diazonium salt, in said aqueous media, with an olefinic substrate having the formula

CH2=C(Z)COOR¹ wherein Z represents —R² or —CH2COOR³ such that R¹, R² and R³ are the same or different and represent —H or an alkyl group —C$_n$H$_{2n+1}$ wherein n=0–20 and the alkyl group is linear or branched, in the presence of (i) a palladium catalyst and (ii) a carboxylic acid having the formula $R^4\text{—}CH_2COOH$ wherein $R^4$ represents H, Cl, $CH_3$ or $C_2H_5$,
at a temperature of from about 0° C. to about 30° C., wherein
(1) the ratio of the olefinic substrate to the arylamine is from about 1:1 to about 2:1;
(2) the palladium catalyst is used in an amount from about 0.05 mole % to 5.0 mole % of the arylamine; and,
(3) the carboxylic acid is used in an about from about 200 mL to about 1000 mL per mole of the arylamine.

2. A process according to claim 1 wherein the nitrous acid is generated from a metal nitrite and a strong mineral acid.

3. A process according to claim 2 wherein the ratio of the mineral acid to the arylamine is from about 1:1 to about 5:1.

4. A process according to claim 3 wherein
a) Ar represents a substituted or unsubstituted phenyl, naphthyl, biphenyl, benzofuranyl, dibenzofuranyl, pyridyl or imidazyl group; and,
b) the palladium catalyst is used in the form of a salt or a complex.

5. A process according to claim 4 wherein
a) the arylamine is a substituted aniline having the formula

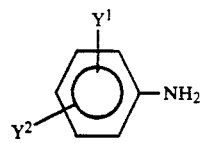

wherein $Y^1$ and $Y^2$ are the same or different and are selected from the group consisting of —H, —R, —COOH, —COOR, —CONH$_2$, —CONHR, —CONR$_2$, —COR, —SO$_3$H, —SO$_3$R, —OR, —CN, —NO$_2$ and —X wherein R represents a linear or branched alkyl group $C_nH_{2n+1}$ wherein n is 1-6, or a phenyl group and —X represents a halogen;
b) Z represents —H; and,
c) the palladium catalyst is selected from the group consisting of sodium chloropalladite, palladium acetate, benzonitrile palladium chloride, palladium nitrate and dibenzylidene acetone palladium.

6. A process according to claim 5 wherein
a) the ratio of the mineral acid to the substituted aniline is from 1:1 to 2:1;
b) the ratio the olefinic substrate to the substituted aniline is from 1:1 to 1.5;1; and,
c) the palladium catalyst is used in an amount from 0.05 mole % to 1.0 mole % of the substituted aniline.

7. A process according to claim 6 wherein a primary amine or an amide is added after the formation of the diazonium salt, in an amount sufficient to remove the nitrous acid.

8. The process according to claim 7 wherein the substituted aniline is p-methoxyaniline, the olefinic substrate is 2-ethylhexyl acrylate, the carboxylic acid is propionic acid and the palladium catalyst is dibenzylidene acetone palladium.

* * * * *